(12) United States Patent
Schneider et al.

(10) Patent No.: US 11,096,663 B2
(45) Date of Patent: Aug. 24, 2021

(54) HAPTIC FEEDBACK FOR ULTRASOUND IMAGE ACQUISITION

(71) Applicant: KONINKLIJKE PHILIPS N.V., Eindhoven (NL)

(72) Inventors: Robert Joseph Schneider, Windham, NH (US); Vijay Parthasarathy, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 449 days.

(21) Appl. No.: 15/300,109

(22) PCT Filed: Mar. 3, 2015

(86) PCT No.: PCT/IB2015/051539
§ 371 (c)(1),
(2) Date: Sep. 28, 2016

(87) PCT Pub. No.: WO2015/150932
PCT Pub. Date: Oct. 8, 2015

(65) Prior Publication Data
US 2017/0181726 A1    Jun. 29, 2017

Related U.S. Application Data

(60) Provisional application No. 61/972,824, filed on Mar. 31, 2014.

(51) Int. Cl.
*A61B 8/00* (2006.01)
*A61B 8/08* (2006.01)
*G06F 3/01* (2006.01)

(52) U.S. Cl.
CPC .............. *A61B 8/42* (2013.01); *A61B 8/4444* (2013.01); *A61B 8/52* (2013.01); *A61B 8/54* (2013.01); *A61B 8/0841* (2013.01); *A61B 8/0883* (2013.01); *A61B 8/4245* (2013.01); *G06F 3/016* (2013.01)

(58) Field of Classification Search
None
See application file for complete search history.

(56) References Cited

U.S. PATENT DOCUMENTS

| 5,645,066 A | 7/1997 | Gandini et al. |
| 2007/0175947 A1 | 8/2007 | Ortiz et al. |

(Continued)

FOREIGN PATENT DOCUMENTS

| JP | H1043182 A | 2/1998 | |
| WO | 2009028354 A1 | 3/2009 | |
| WO | WO-2009028354 A1 * | 3/2009 | ............... A61B 8/00 |

*Primary Examiner* — Angela M Hoffa
*Assistant Examiner* — Younhee Choi

(57) ABSTRACT

A system for providing navigational guidance to a sonographer acquiring images may provide haptic feedback to the sonographer. The haptic feedback may be provided through an ultrasonic probe or a separate device. Haptic feedback may include vibrations or other sensations provided to the sonographer. The system may analyze acquired images and determine the location of acquisition and compare it to a desired image based, at least in part, on the acquired image. The system may then provide the haptic feedback to guide the sonographer to move the ultrasonic probe to the location to acquire the desired image.

15 Claims, 5 Drawing Sheets

Operational flow chart

(56) References Cited

U.S. PATENT DOCUMENTS

| | | | |
|---|---|---|---|
| 2008/0021321 A1 | 1/2008 | Guracar et al. | |
| 2010/0152586 A1 | 6/2010 | Grant et al. | |
| 2010/0168576 A1 | 7/2010 | Poland et al. | |
| 2010/0179587 A1* | 7/2010 | Grant | A61B 17/2909 606/205 |
| 2012/0010506 A1* | 1/2012 | Ullrich | A61B 1/00045 600/440 |
| 2012/0108965 A1 | 5/2012 | Lazebnik | |
| 2013/0178744 A1* | 7/2013 | Kierulf | A61B 8/467 600/459 |
| 2013/0296707 A1 | 11/2013 | Anthony et al. | |
| 2013/0331664 A1 | 12/2013 | Gilad-Gilor | |
| 2014/0132568 A1 | 5/2014 | Hirose et al. | |

* cited by examiner

Haptic apparatus

Operational flow chart

HAPTIC FEEDBACK FOR ULTRASOUND IMAGE ACQUISITION

This application is the U.S. National Phase application under 35 U.S.C. § 371 of International Application No. PCT/IB2015/051539, filed on Mar. 3, 2015, which claims the benefit of Provisional Application Ser. No. 61/972,824, filed Mar. 31, 2014. These applications are hereby incorporated by reference herein.

TECHNICAL FIELD

This invention relates to medical ultrasonic imaging systems and, in particular, to haptic feedback devices to aid sonographers acquiring ultrasound images.

BACKGROUND

A difficulty plaguing ultrasound image acquisitions is that of ultrasound probe navigation. As the acquired ultrasound images do not have a fixed reference frame, it may be difficult for a sonographer to know at any given time where to move the probe to acquire images of an object of interest. Often the knowledge of how and where to move the probe to acquire an image of a particular object of interest is gained from significant experience. There is increasing demand for imaging applications to provide not only qualitative assessments, but also quantitative measurements. These quantitative measurements may be manual, semi-automatic, or fully automatic computer analysis of acquired images. Image quality and correct field of view are even more critical in these automatic analysis applications. These increased demands for image acquisition may be challenging to meet, even for skilled sonographers.

As real-time segmentation algorithms are becoming more prevalent, the possibility of providing real-time navigational feedback to the sonographer to indicate regions in which the sonographer may want to acquire more image data is becoming a greater possibility. However, translating this navigational information to the sonographer in a meaningful way is not trivial. While information about where to move the probe could be shown on the images displayed on a monitor, it may not be obvious to the sonographer how to translate or rotate the probe so as to acquire images in the desired regions. Furthermore, as it is desirable for the sonographer to continuously observe the acquired images displayed on the monitor, any navigational information about where to move the probe needs to be translated to the sonographer without the use of visual cues solely on the displayed images or on the probe itself.

SUMMARY OF THE INVENTION

Through the use of a haptic information system, real-time navigational feedback may be provided to the sonographer in an intuitive fashion.

According to one illustrative embodiment of the invention disclosure, a system for providing navigational guidance to a sonographer may include an ultrasound probe that may transmit and receive an echo signal, an acquisition system that may receive a signal from the ultrasound probe corresponding to the echo signal received by the ultrasound probe and produce an image, a display system that may receive the image from the acquisition system, the display system may include an anatomical analytical model that may analyze the image and transmit data to a tracking processor that may calculate a movement of the ultrasound probe to acquire an image based at least in part, on data received from the anatomical model, and a navigation instruction generator that may convert the movement calculated by the tracking processor into navigational instructions that may be sent to a haptic apparatus included with the ultrasound probe which may be operate a haptic feedback device based at least in part on the navigational instructions, and the haptic feedback device may provide haptic navigational instructions to the sonographer. The haptic apparatus may comprise a plurality of haptic feedback devices distributed across an inner surface of the haptic apparatus. The haptic apparatus may operate the plurality of haptic feedback devices in accordance with a navigational instruction set where a combination of haptic feedback devices operated simultaneously may correspond to a navigational instruction. The haptic feedback device may be a motor that may provide vibration. The haptic apparatus may further include a force sensor. The system may receive data from the force sensor and calculate a movement of the ultrasound probe to acquire an image based at least in part on the data received from the force sensor. The system may operate continually to provide the sonographer with navigational guidance. The tracking processor may receive physiological data and calculate a movement of the ultrasound probe to acquire an image based, at least in part on the physiological data.

According to another disclosed embodiment of the present invention, a method of providing navigational guidance to a sonographer may include analyzing an image acquired by an ultrasound prove with an anatomical analytical model; calculating movement of the ultrasound probe based at least in part on the analysis of the image; and providing haptic feedback through the ultrasound probe to navigate the ultrasound probe. The method may further include analyzing a second image acquired by the ultrasound probe with the anatomical model to determine sufficiency of the image. The method may further include providing a signal to the sonographer when the sufficient image has been acquired. The signal may be a visual signal. The method may further include transmitting instructions to a haptic apparatus attached to the ultrasound probe and activating haptic feedback devices in the haptic apparatus to provide the haptic feedback to the sonographer.

According to a further embodiment according to the principles of the invention, a non-transitory computer-readable medium with instructions for navigational guidance in acquiring an ultrasound image stored thereon to be executed by one or more processors, which instructions when executed may cause the one or more processors to emit ultrasound waves from an ultrasound probe, generate an image from an echo signal received by the ultrasound probe, analyze the image to determine if the image is sufficient, calculate a required movement of the ultrasound probe to obtain a sufficient image, generate navigational instructions based on the required movement, and transmit navigational instructions to a haptic apparatus.

DETAILED DESCRIPTION OF PREFERRED EMBODIMENTS

In the following detailed description, for purposes of explanation and not limitation, illustrative embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the illustrative embodiments. Such methods and apparatus are within the scope of the present teachings.

Figure 1:
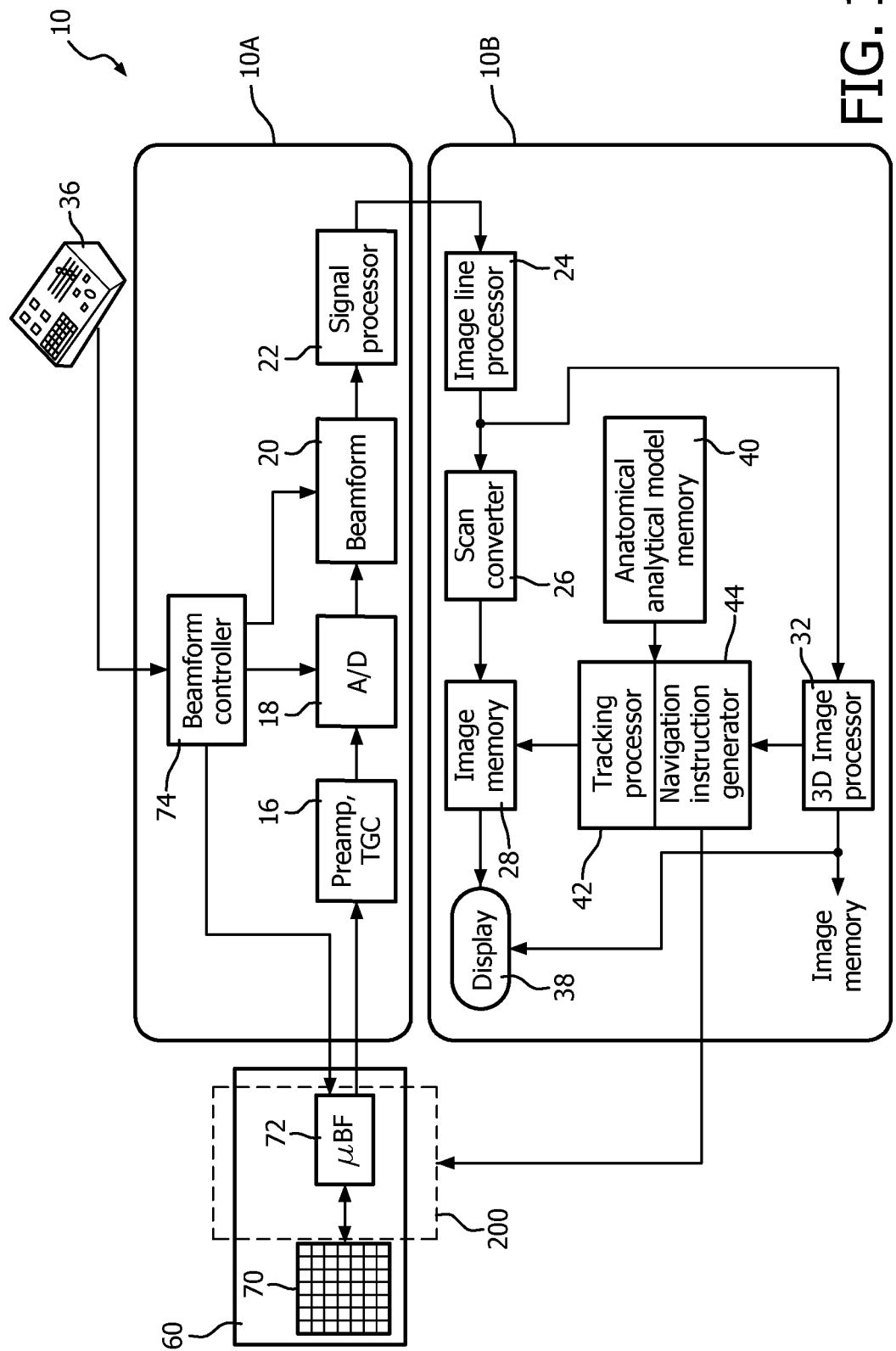
FIG. 1 is a block diagram of a medical ultrasound system according to an illustrative embodiment of the invention.

Referring to FIG. 1, an ultrasonic imaging system according to an embodiment of the present invention is shown in block diagram form. The ultrasound system is configured by two subsystems, a front end acquisition subsystem 10A and a display subsystem 10B. An ultrasound probe 60 is coupled to the acquisition subsystem which includes a two-dimensional matrix array transducer 70 and a micro-beamformer 72. The micro-beamformer contains circuitry which control the signals applied to groups of elements ("patches") of the array transducer 70 and does some processing of the echo signals received by elements of each group.

The acquisition subsystem 10A includes a beamform controller 74 which is responsive to a user control 36 and provides control signals to the microbeamformer 72, for example, instructing the probe as to the timing, frequency, direction and focusing of transmit beams. The beamform controller also controls the beamforming of echo signals received by the acquisition subsystem by its control of analog-to-digital (A/D) converters 18 and a system beamformer 20. Echo signals received by the probe are amplified by preamplifier and TGC (time gain control) circuitry 16 in the acquisition subsystem, then digitized by the A/D converters 18. The digitized echo signals are then formed into fully steered and focused beams by the system beamformer 20. The echo signals are then processed by a signal processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The image is then stored in an image buffer or memory 28 from which it can be displayed on a display 38. The image in memory 28 is also overlaid with graphics to be displayed with the image, which are generated by a graphics generator (not shown) which is responsive to the user control 36. Individual images or image sequences can be stored in a cine memory (not shown) during capture of image loops or sequences.

For real-time volumetric imaging the display subsystem 10B also includes a 3D image rendering processor 32 which receives image lines from the image line processor 24 for the rendering of real-time three dimensional images. The 3D images can be displayed as live (real time) 3D images on the display 38 or coupled to the image memory 28 for storage of the 3D data sets for later review and diagnosis.

In accordance with the principles of the present invention the display subsystem may also include an automated anatomical analytical model stored in memory 40. An example of such an anatomical analytical model is the Heart Model technology described in U.S. patent application Ser. No. 13/884,617 "Identifying individual sub-regions of the cardiovascular system for calcium scoring." This technology may be able to rapidly segment a majority of the cardiac anatomy (chambers, vasculature, etc.) from 3D ultrasound volumes using a model-based approach, and in doing so, may determine quickly those areas where sufficient or insufficient image data was found. A second example of an anatomical analytical model is a model to predict the deformation of a biopsy needle to aid sonographers in keeping the tip of the needle in the field of view of the transducer 70 during a biopsy procedure. In non-medical applications, the anatomical model may be replaced with any appropriate model for the object to be imaged for determining areas where sufficient or insufficient image data are found.

Data from the analytical model 40 may be transmitted to the tracking processor 42. The tracking processor 42 may predict where the ultrasound probe 60 should move relative to its current position to obtain the desired image based at least in part on data provided from the analytical model 40 and transmit the required probe movement to the navigation instruction generator 44, which generates navigation instructions that are transmitted to a haptic apparatus 200, described in more detail below. The tracking processor 42 could indicate on the display 38 where more image data is needed and indicate how to move the probe 60 relative to its current position. However, due to the symmetry of the probe 60, the sonographer may not always know exactly what movements of the probe coincide with the necessary translations and/or rotations required. While visual cues on the ultrasound probe 60 (for example, LEDs) could be used to indicate to the sonographer how to move the probe 60, it is desirable to have the sonographer maintain constant observation of the displayed images, especially for interventional cases where the relative position of anatomy and tools/instruments/devices are being maneuvered within the field of view.

Figure 2:
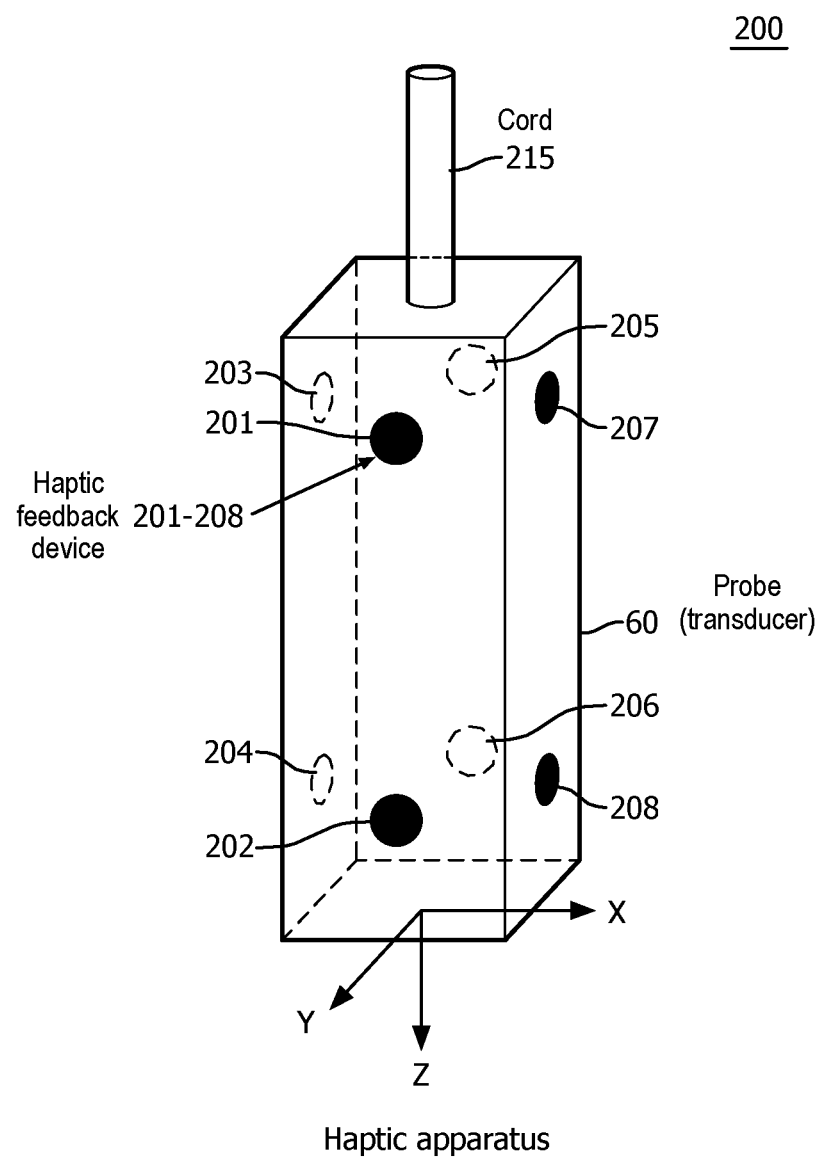
FIG. 2 is a block diagram of a haptic apparatus according to an illustrative embodiment of the invention.

FIG. 2 illustrates an embodiment of a haptic apparatus 200 that may be attached to the exterior of the ultrasound probe 60 or integrated inside the enclosure of ultrasound probe 60. The haptic apparatus 200 provides an intuitive and non-intrusive way to communicate to the sonographer the information from the tracking processor 42. The haptic apparatus 200 may be configured to provide physical sensations to the sonographer's hand holding the ultrasound probe 60. These physical sensations for conveying where the ultrasound probe 60 should be moved as calculated by the tracking processor 42 are haptic navigational instructions. The haptic apparatus 200 comprises a plurality of haptic feedback devices 201-208. Eight haptic feedback devices are pictured in this illustrative embodiment, but more or less could be used. The haptic feedback devices 201-208 may be motors that generate a vibration that can be felt by a sonographer holding the ultrasound probe 60. Power and navigation instructions from the navigation instruction generator 44 are delivered by a cord 215.

The desired movement of the ultrasound probe 60 calculated by the tracking processor 42 may be translated into a sequence of vibrational pulses sent to one or more haptic feedback devices 201-208 by the navigation instruction generator 44. The instructions may be translated into causing vibration at one or more haptic feedback devices 201-208 and/or different vibrational strengths at one or more haptic feedback devices 201-208. The pattern or sequence of activating the haptic feedback devices 201-208 may be determined by a pre-determined navigation instruction set.

Figure 3:
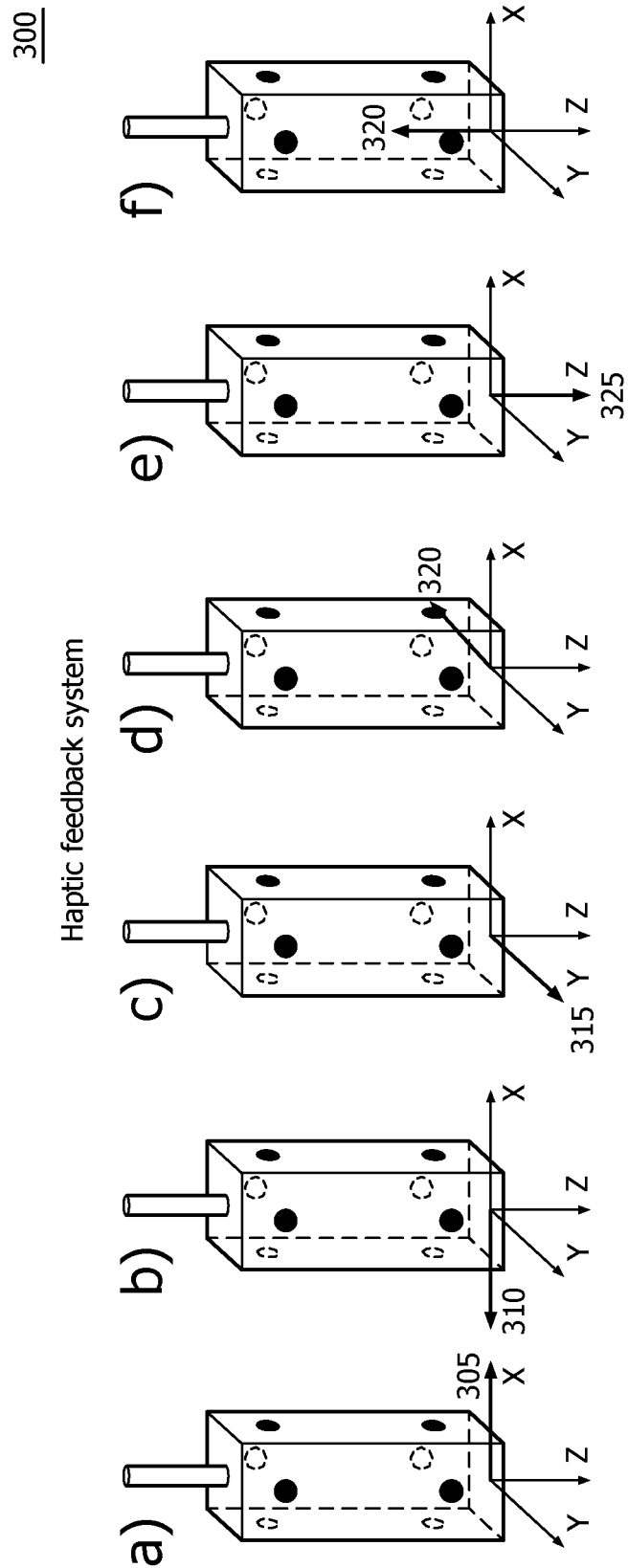
FIG. 3 is a block diagram of a navigational instruction set according to an illustrative embodiment of the invention.
Figure 3:
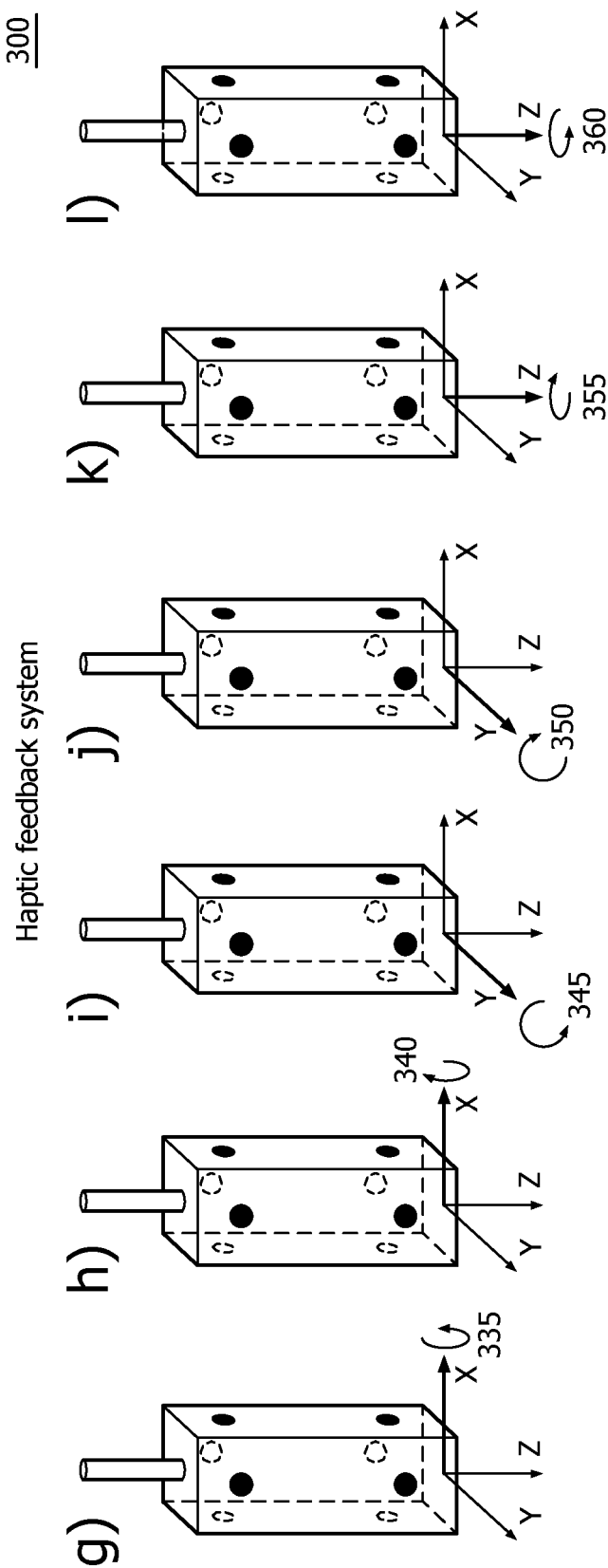

An example of a navigation instruction set 300 is shown in FIG. 3. Other navigation instruction sets may be possible. All directions described below are from the perspective of the reader, not the haptic apparatus 200 or a sonographer. Instructions (a)-(f) describe how to move the ultrasound probe 60 in a 3D space. In (a), two haptic feedback devices 207, 208 on the right of the haptic apparatus 200 vibrate to indicate to the sonographer to move the probe 60 in direction 305 along the x-axis to the right. In (b), two haptic feedback devices 203, 204 on the left side of the haptic apparatus 200 vibrate to indicate to the sonographer to move the probe 60 in direction 310 along the x-axis to the left. In (c), two haptic feedback devices 201, 202 on the front of the haptic apparatus 200 vibrate to indicate to the sonographer to move the probe 60 in direction 315 along the y-axis out of the page. In (d), two haptic feedback devices 205, 206 on the back of the haptic apparatus 200 vibrate to indicate to the sonographer to move the probe 60 in direction 320 along the y-axis into the page. In (e), four haptic feedback devices 202, 204, 206, 208 on the lower portion of the haptic apparatus 200 vibrate to indicate to the sonographer to move the probe downward in direction 325 along the z-axis. In (f), four haptic feedback devices 201, 203, 207 on the upper portion of the haptic apparatus 200 vibrate to indicate to the sonographer to move the probe 60 upward in direction 330 along the z-axis.

Instructions (g)-(l) describe how to rotate the ultrasound probe 60 to adjust the angle at which the transducer 70 is incident to the object being imaged. In (g), the front lower haptic feedback device 202 and the upper back haptic feedback device 205 vibrate to indicate to the sonographer to rotate the probe 60 in direction 335 counterclockwise around the x-axis. In (h) the front upper haptic feedback device 201 and the lower back haptic feedback device 206 vibrate to indicate to the sonographer to rotate the probe 60 in direction 340 clockwise around the x-axis. In (i) the lower left haptic feedback device 204 and the upper right haptic feedback device 207 vibrate to indicate to the sonographer to rotate the probe 60 in direction 345 counterclockwise around the y-axis. In (j), the upper left haptic feedback device 203 and the lower right haptic feedback device 208 vibrate to indicate to the sonographer to rotate the probe 60 in direction 350 clockwise around the y-axis. In (k) the upper front haptic feedback device 201 and the lower left haptic feedback device 204 vibrate to indicate to the sonographer to rotate the probe 60 in direction 355 clockwise around the z-axis. Finally, in (l) the upper front haptic feedback device 201 and the lower right haptic feedback device 208 vibrate to indicate to the sonographer to rotate the probe 60 in direction 360 counter clockwise around the z-axis.

In another embodiment of the invention, the haptic apparatus 200 may also include one or more force sensors (not shown) adjacent to the transducer 70. Data from the force sensors may be sent to the tracking processor 42, and the navigation instruction generator 44 may provide instructions to the sonographer via the haptic apparatus 200 to increase or decrease pressure applied with the probe. Other physiological data that could be collected and provided to the tracking processor 42 to provide haptic feedback to the sonographer include respiration rate and ECG signals. This data could be collected by additional sensors integrated into the haptic apparatus 200 or may be separate devices configured to transmit data to the tracking processor 42.

Figure 4:
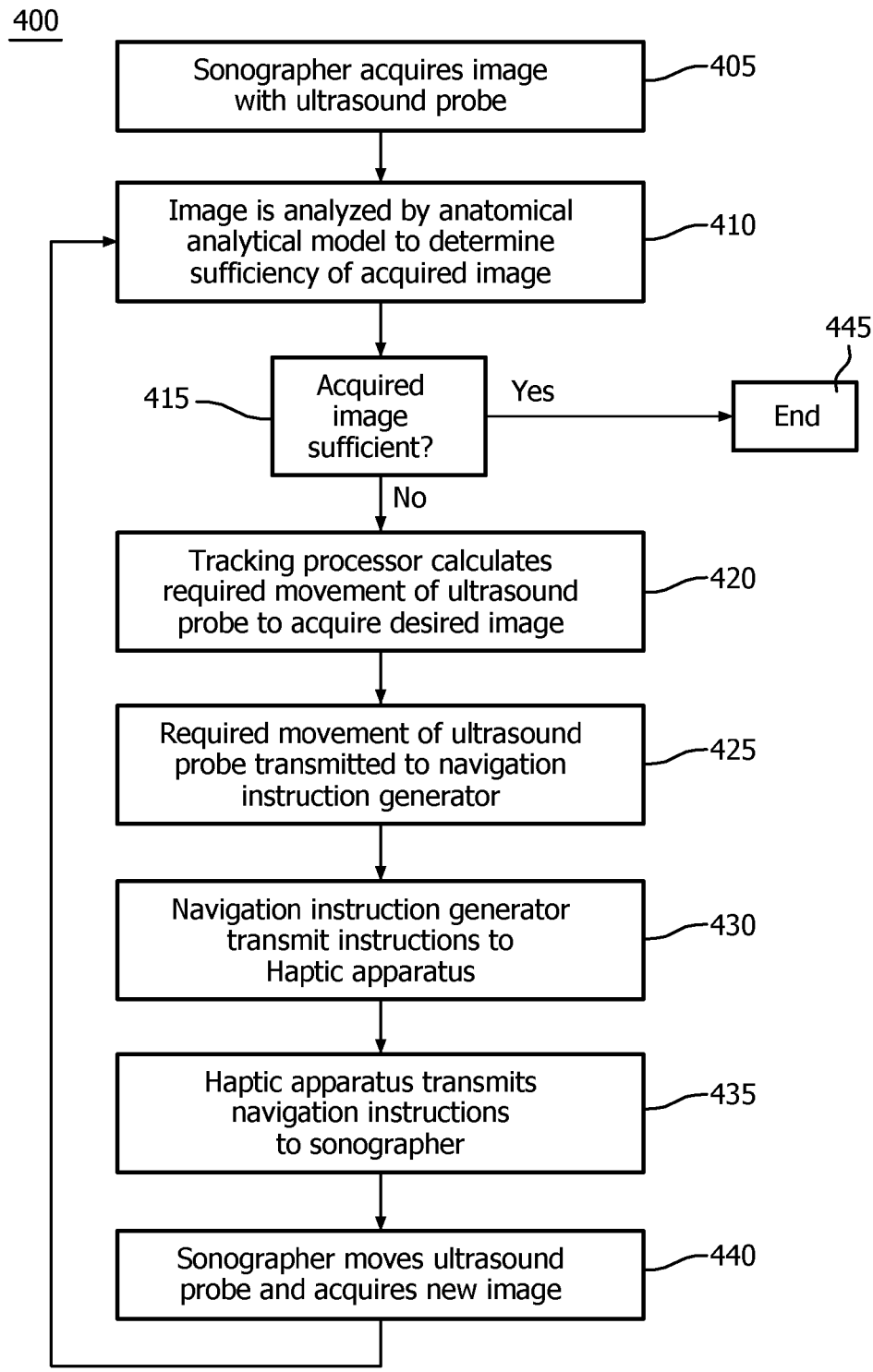
FIG. 4 is a flow chart of the operation of an illustrative embodiment of the invention.

FIG. 4 is a flow diagram of an example process of acquiring an image with an embodiment of the invention. A sonographer acquires an image 405 with the ultrasound probe 60. The anatomical analytical model 40 analyzes the image to determine if the image is sufficient 410. If the image is determined to be sufficient, the process terminates at 445. For an image to be sufficient, the image may be of the desired quality and at the correct field of view. The sonographer may be alerted to the sufficiency of the image by a visual signal on the display 38 or other signal. If the anatomical analytical model 40 determines that the image is insufficient, the tracking processor 42 calculates the required movement of the ultrasound probe 60 to acquire the desired image 420. The required movement of the ultrasound probe 60 is transmitted to the navigation instruction generator 44, and the required movement is translated into instructions to be provided to the sonographer 425. The navigation instruction generator 44 transmits instructions to the haptic apparatus 200 at step 430. The haptic apparatus transmits the navigation instructions to the sonographer 435 using the haptic feedback devices 201-208 utilizing an instruction set such as the one illustrated in FIG. 3. The sonographer may move the ultrasound probe 60 based, at least in part, on the instructions provided by the haptic apparatus 200, and acquires a new ultrasound image 440. This new image is then transmitted to the anatomical analytical model for analysis 410. The process repeats until a sufficient image is acquired by the sonographer.

In various embodiments where the above-described systems and/or methods are implemented using a programmable device, such as a computer-based system or programmable logic, it should be appreciated that the above-described systems and methods can be implemented using any of various known or later developed programming languages, such as "C", "C++", "FORTRAN", Pascal", "VHDL" and the like.

Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform the above-described systems and/or methods.

For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

What is claimed is:

1. A system for providing navigational instructions, the system comprising:
an ultrasound probe configured to transmit ultrasound and receive an echo signal;
a plurality of haptic feedback devices configured to provide haptic feedback to a sonographer, wherein the plurality of haptic feedback devices are arranged at different locations on the ultrasound probe, wherein the plurality of haptic feedback devices includes a first plurality of haptic feedback devices on a first side of the ultrasound probe and a second plurality of haptic feedback devices on a second side of the ultrasound probe opposite the first side;
an acquisition system including a beamform controller and a beamformer, the acquisition system configured to receive a signal from the ultrasound probe corresponding to the echo signal received by the ultrasound probe and produce a first image from the acquired signals at a first location; and
a display system comprising at least one processor configured to receive the image from the acquisition system, determine a target location for acquiring a target image based on an anatomical model and the first location, and transmit the navigational instructions to one or more of the plurality of haptic feedback devices when the display system determines that the first location does not correspond to the target location, wherein the navigational instructions correspond to an activation pattern for activating the one or more of the plurality of haptic feedback devices, wherein the activation pattern is configured to guide the sonographer in moving the ultrasound probe to the target location for acquiring a second image of the target location, and wherein the activation pattern is selected from a first activation pattern that causes activation of the first plurality of haptic feedback devices together upon the display system determining that the ultrasound probe should be moved in a direction toward the first side, a second activation pattern that causes activation of the second plurality of haptic feedback devices together upon the display system determining that the ultrasound probe should be moved in a direction toward the second side, and a third activation pattern that causes activation of a subset of the first plurality of haptic devices or the second plurality of haptic devices upon the display system determining that the ultrasound probe should be rotated; and
wherein the plurality of haptic feedback devices are configured to activate in accordance with the activation pattern received from the display system.

2. The system of claim 1, wherein the plurality of haptic feedback devices are distributed across an inner surface of a haptic apparatus attached to an exterior of the ultrasound probe or integrated inside an enclosure of the ultrasound probe.

3. The system of claim 2, wherein the first plurality of haptic feedback devices are elevationally distributed along the first side and the second plurality of haptic feedback devices are elevationally distributed along the second side, and wherein the navigational instructions are selected from instructions further including fourth activation pattern configured to activate one of the first plurality of haptic feedback devices together with one of the second plurality of haptic feedback devices located at a corresponding elevation upon determining that pressure applied with the ultrasound probe should be increased or decreased.

4. The system of claim 1, wherein at least one of the plurality of haptic feedback devices includes a motor, wherein the motor is configured to provide multiple levels of vibration strength.

5. The system of claim 1, wherein the one or more haptic feedback devices are caused to vibrate in accordance with the respective activation pattern.

6. The system of claim 1, wherein the plurality of haptic feedback devices are integrated into the ultrasound probe.

7. The system of claim 1, wherein the display system continually analyzes images produced by the acquisition system to continually provide navigational guidance.

8. The system of claim 1, further comprising a display configured to display the first image and wherein the display is further configured to display a message upon a determination that the first image corresponds to the target image.

9. The system of claim 1, wherein the plurality of haptic feedback devices are part of a haptic apparatus further comprising a force sensor, and wherein the display system is further configured to receive data from the force sensor and calculate a movement of the ultrasound probe to acquire an image of the target location based, at least in part, on the data received from the force sensor.

10. The system of claim 1, wherein the display system is further configured to receive physiological data and calculate a movement of the ultrasound probe to acquire an image based, at least in part, on the physiological data.

11. A method of providing navigational instructions, the method being executed by a processor and comprising steps of:
analyzing an image acquired by an Ultrasound probe at a first location with an anatomical analytical model to compare the first location to a target location for acquiring a target image of a subject;
calculating, based at least in part on the analysis of the image, a movement of the ultrasound probe to the target location for acquiring the target image;
transmitting the navigational instructions to one or more of a plurality of haptic feedback devices configured to provide haptic feedback to a sonographer, wherein the plurality of haptic feedback devices are arranged at different locations on the ultrasound probe, each of the plurality of haptic feedback devices providing a vibration when activated, wherein the plurality of haptic feedback devices includes a first plurality of haptic feedback devices on a first side of the ultrasound probe and a second plurality of haptic feedback devices on a second side of the ultrasound probe opposite the first side, and wherein the navigational instructions correspond to an activation pattern for activating the one or more of the plurality of haptic feedback devices based on the calculated movement of the ultrasound probe, wherein the activation pattern is selected from a first activation pattern that causes activation of the first plurality of haptic feedback devices together upon determining, based on the calculated movement of the ultrasound probe, that the ultrasound probe should be translated in a direction toward the first side, a second activation pattern that causes activation of the second plurality of haptic feedback devices together upon determining, based on the calculated movement of the ultrasound probe, that the ultrasound probe should be translated in a direction toward the second side, and a third activation pattern that causes activation of a subset of the first plurality of haptic devices or the second plurality of haptic devices upon determining, based on the calculated movement of the ultrasound probe, that the ultrasound probe should be rotated; and activating the one or more of the plurality of haptic feedback devices in accordance with the navigational instructions to provide navigational guidance to the sonographer.

12. The method of claim 11, further comprising analyzing a second image acquired by the ultrasound probe to determine whether further haptic feedback should be provided via the plurality of haptic feedback devices.

13. The method of claim 12, further comprising providing a signal to the sonographer upon determination that no further haptic feedback should be provided.

14. The method of claim 11, wherein the one or more of the plurality of haptic feedback devices provide different strengths of vibrations when activated.

15. A non-transitory computer-readable medium with instructions for navigational guidance in acquiring an ultrasound image stored thereon to be executed by one or more processors, wherein the instructions, when executed, cause the one or more processors to:

emit ultrasound waves from an ultrasound probe operatively associated with a plurality of haptic feedback devices configured to provide haptic feedback to a sonographer and are arranged at different locations on the ultrasound probe, wherein the plurality of haptic feedback devices includes a first plurality of haptic feedback devices on a first side of the ultrasound probe and a second plurality of haptic feedback devices on a second side of the ultrasound probe opposite the first side;

generate an image from an echo signal received by the ultrasound probe at a first location;

compare the first location to a target location for acquiring a target image of a subject based on an anatomical analytical model;

when the image does not correspond to the target image, calculate a required movement of the ultrasound probe to the target location;

generate an activation pattern based on the required movement, wherein the activation pattern is selected from a first activation pattern that causes activation of the first plurality of haptic feedback devices together upon a determination that the ultrasound probe should be moved in a direction toward the first side, a second activation pattern that causes activation of the second plurality of haptic feedback devices together upon a determination that the ultrasound probe should be moved in a direction toward the second side, and a third activation pattern that causes activation of a subset of the first plurality of haptic devices or the second plurality of haptic devices upon a determination that the ultrasound probe should be rotated; and transmit the activation pattern to the one or more of the plurality of haptic feedback devices to cause the one or more of the plurality of haptic feedback devices to activate in accordance with the activation pattern.

* * * * *